United States Patent [19]

Sheer et al.

[11] Patent Number: 5,124,041
[45] Date of Patent: Jun. 23, 1992

[54] BIOMOLECULE SAMPLE IMMOBILIZATION

[75] Inventors: Donald G. Sheer, Foster City; Michael L. Kochersperger, Menlo Park, both of Calif.

[73] Assignee: Applied Biosystems, Inc., Foster City, Calif.

[21] Appl. No.: 697,916

[22] Filed: May 1, 1991

Related U.S. Application Data

[63] Continuation of Ser. No. 386,847, Jul. 28, 1989, abandoned.

[51] Int. Cl.$^5$ .............. B01D 61/14; B01D 15/08; B01D 69/12
[52] U.S. Cl. .............. 210/641; 210/650; 210/651; 210/691; 210/781; 210/782; 210/806; 210/321.64; 210/321.67; 210/321.84; 210/359; 210/502.1; 210/514; 422/56; 422/60; 422/61; 422/72; 422/101; 435/6; 436/501; 436/170; 436/178; 530/415; 935/77
[58] Field of Search .............. 210/641, 650, 651, 690, 210/691, 781, 782, 787, 789, 321.64, 321.67, 321.84, 359, 502.1, 514, 515, 806; 422/56, 58, 60, 61, 72, 100, 101, 102; 435/6; 436/165, 169, 170, 501, 177, 178, 180; 530/412, 413, 415, 427; 935/9, 77, 78

[56] References Cited

U.S. PATENT DOCUMENTS

| | | | |
|---|---|---|---|
| 3,493,503 | 2/1970 | Mass | 210/927 |
| 3,670,892 | 6/1972 | Baerg et al. | 210/502.1 |
| 4,021,352 | 5/1977 | Sarstedt | 210/789 |
| 4,522,713 | 6/1985 | Nussbaumer et al. | 210/359 |
| 4,683,202 | 7/1987 | Mullis | 435/91 |
| 4,722,792 | 2/1988 | Miyagi et al. | 210/515 |
| 4,797,260 | 1/1989 | Parker | 422/101 |
| 4,812,293 | 3/1989 | McLaurin et al. | 422/101 |
| 4,826,771 | 5/1989 | Eggersten | 435/6 |
| 4,832,851 | 5/1989 | Bowers et al. | 210/321.67 |
| 4,859,336 | 8/1989 | Savas et al. | 422/101 |

Primary Examiner—W. Gary Jones
Attorney, Agent, or Firm—Joseph H. Smith; Ronald E. Grubman; Donald R. Boys

[57] ABSTRACT

A filter system for separating and binding biomolecules contained in a solution includes a first filter means for selectively passing components of the solution that are smaller than the biomolecules, thereby concentrating the biomolecules in the solution. Also included is a binding membrane means having an affinity for the biomolecules for binding the biomolecules to the binding membrane means, with the binding membrane means being located where the biomolecules are concentrated by the first filter means. In the preferred mode, the binding membrane means is chosen to selectively bind the biomolecule of interest. According to a preferred method of the invention, biomolecules from a sample volume are bound to a binding membrane by urging the sample volume against a biomolecule-binding support membrane that is in contact with a cut-off filter membrane such that the sample volume will pass through the biomolecule-binding support membrane before passing through the cut-off filter membrane. The concept is to concentrate the biomolecules of interest by means of the cut-off membrane in the vicinity of the binding membrane, thereby increasing the binding yield on the binding membrane. In the preferred mode, the sample volume is urged against the binding membrane by centrifugation.

10 Claims, 4 Drawing Sheets

BIOMOLECULE SAMPLE IMMOBILIZATION

CROSS REFERENCE TO RELATED APPLICATION

This is a continuation of application Ser. No. 386,847, filed Jul. 28,1989, now abandoned.

FIELD OF THE INVENTION

The present invention is in the area of apparatus and methods for handling biomolecules during analytical chemical separation processes. The invention relates particularly to improvements in yield and efficiency in binding these biomolecules to supports for subsequent processing.

BACKGROUND OF THE INVENTION

In processes requiring the separation and analysis of biomolecules such as proteins, nucleic acids, lipids, and carbohydrates, it is often convenient to bind the biomolecules to a solid matrix at some point in the process flow. Such binding allows materials that might be troublesome in further analysis to be removed while retaining the biomolecule or biomolecules of interest. As an example, a well-known technique for separating proteins in a protein mixture is by sodium dodecyl sulfate-polyacrylamide gel electrophoresis, known in the art as SDS-PAGE. A potential problem in the overall procedure is that SDS and other materials in the sample after electrophoresis can interfere with subsequent analysis. If the proteins can be bound to a support, the SDS and other unwanted chemicals or reagents can be relatively easily removed. A sample support with the sample proteins bound thereto is also convenient for further handling of sample in analytical techniques such as, for example, amino acid and sequence analysis. To be useful, such a support needs to be compatible with the organic solvents, acids, and bases used in amino acid analysis and sequencing.

A variety of support matrices and attachment chemistries have been developed in the art, depending on the particular biomolecule to be separated. These materials include, for example, nitrocellulose, DEAE-cellulose, derivatized glass beads, derivatized nylon, parchment, macrocyclic polyethers, polyvinylbutyral resin, polyvinylalcoholcollagen, polyvinylidene difluoride, and other polymers. As a specific example, diisothiocyanate (DITC) derivitized glass beads have been used as well as DITC functionalized glass fiber sheets. These matrices both react with the epsilon-amino groups of the lysine side chains of peptides and proteins. Subsequent analysis of proteins resolved by gel electrophoresis can be performed by blotting or electroblotting directly onto DITC-activated glass fiber sheets with covalent attachment occurring during the transfer. Disadvantages are that the glass fiber sheets are fragile in subsequent handling, and it is difficult to detect the protein molecules on the glass surface. More importantly, however, is that they have a relatively low protein binding capacity.

More recently polyvinylidene difluoride (PVDF) membranes have been used in blotting and electroblotting, and have proved to be relatively more useful than glass supports. The membrane bound molecules can be readily visualized with a variety of compound, for example, by staining, such as with coomassie blue for proteins. Also PVDF membranes with bound proteins can be used as supports in state-of-the-art protein sequencing equipment, because the PVDF material is compatible with the materials and conditions encountered in such equipment. Furthermore, the binding to PVDF is typically reversible, so that the bound molecules can be easily removed from the membrane for subsequent analysis.

Even more recently the DITC attachment chemistry has been combined with PVDF membranes to produce membranes with even better properties for binding of biomolecules than PVDF alone. An example is the Immobilon TM PVDF Transfer Membrane developed and sold by Millipore Corporation of Bedford MA, which is a hydrophobic membrane having generally a broad affinity for proteins. Another membrane, Immobilon N TM PVDF Transfer Membrane, also developed and sold by Millipore Corporation, is derivatized to be hydrophilic and hence is used primarily as a DNA binding substrate. Other examples of some of the more recent developments include such membranes as ProBlott TM available from Applied Biosystems (another PVDF membrane), and derivatized nitrocellulose. Although these membranes have emerged as preferred membranes for electroblotting/sequencing of different kinds of biomolecules, there are still several problems that can cause low recoveries and variable results. The problems most often encountered during electroblotting or in other sample adsorption techniques onto these membranes include a variability in electrotransfer for different proteins, long times required (as long as 24 hours) for adsorption of molecules onto the membranes from solution, variable results in recovery due to selectivity, and staining/destaining methods which reduce sequencing yields. The blotting techniques, moreover, are not very useful for small amounts of sample and sample in free solution.

What is clearly needed is a method and apparatus for binding biomolecules to solid supports that is useful for small amounts of sample in large volumes; that is rapid; that is not dependent on electrotransfer and does not exhibit the variability observed in electroblotting; that, for proteins is not selective (as shown in electroblotting); and is not dependent on staining techniques which cause sample loss (ie. to find the sample).

SUMMARY OF THE INVENTION

In accordance with preferred embodiments of the invention, a filter system for separating and binding biomolecules contained in a solution is presented having a first filter means for selectively passing components of the solution that are smaller than the biomolecules, thereby concentrating the biomolecules in the solution. Also included is a binding membrane means having an affinity for the biomolecules for binding the biomolecules to the binding membrane means, with the binding membrane means being located where the biomolecules are concentrated by the first filter means. In the preferred mode, the binding membrane means is chosen to selectively bind the biomolecule of interest. At the present time, examples of these binding membranes include PVDF, derivatized PVDF, nitrocellulose, DEAE-cellulose, derivatized glass beads, nylon, derivatized nylon, parchment, macrocyclic polyethers, polyvinylbutyral resins, polyvinylalcoholcollagen, and polyvinylidene difluoride, other polymers; and congugates or complexes thereof.

According to a preferred method of the invention, biomolecules from a sample volume are bound to a binding membrane by urging the sample volume against a biomolecule-binding support membrane that is in contact with a cut-off filter membrane such that the sample volume will pass through the biomolecule-binding support membrane before passing through the cut-off filter membrane. The concept is to concentrate the biomolecules of interest by means of the cut-off membrane in the vicinity of the binding membrane, thereby increasing the binding yield on the binding membrane. In the preferred mode, the sample volume is urged against the binding membrane by centrifugation. However, other means can also be used. Once the biomolecules of interest are bound to the binding membrane, they can be analyzed in situ, or they can be removed from the binding support for further analysis or use.

Applications of the method abound. For example, since the process provides a straightforward isolation technique for DNA, small samples of DNA can be easily isolated and used in subsequent experiments. Further, clinical applications become immediately apparent since once the DNA is isolated it can be subjected to a polymerase chain reaction for amplification, and subsequent processing. Another application is in the field of assays for DNA-binding proteins. There the DNA-binding proteins are first bound to the binding support according to the method of the invention. Then, the DNA can be bound to the protein on the support and the system can be evaluated for binding efficiency.

DESCRIPTION OF THE PREFERRED EMBODIMENTS

Figure 1:
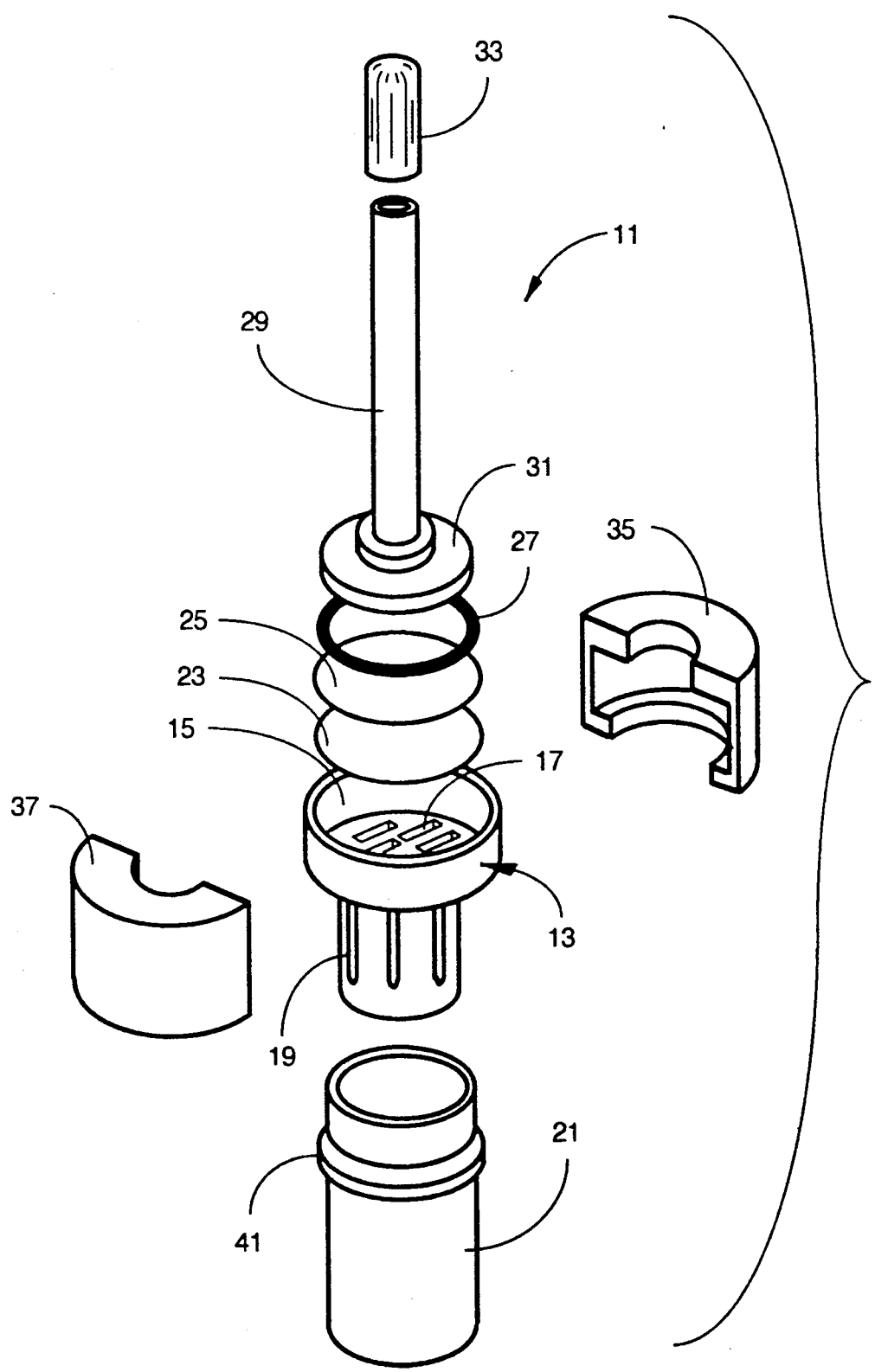
FIG. 1 is an exploded perspective view of an apparatus according to a preferred embodiment.

FIG. 1 is an exploded perspective view of an apparatus according to a preferred embodiment for facilitating adsorption of biomolecules onto solid matrix supports by forced filtration. Microfuge assembly 11 is configured for processing in a swinging bucket rotor, forcing filtration by centrifugation, although other methods of forced filtration could also be used, for example pressure transfer or vacuum transfer. Assembly 11 is for relatively large bimolecule -bearing sample solutions, generally above 10 microgram.

In the preferred mode, assembly 11 filter base 13 has a sample cavity 15 about 14 mm. in diameter and about 5mm. deep. There are a plurality of openings, such as opening 17, that lead through the bottom of the sample cavity into a lower cylindrical portion 19. Portion 19 fits into cylindrical reservoir 21 which serves to collect filtrate during centrifugation.

A cut-off filter membrane 23, in the preferred mode having a diameter of about 14 mm., fits in the sample cavity in filter base 13 and covers the openings through the filter base. In general, the filter membrane serves as a sieve of a desired pore size depending on the particular biomolecule that has been chosen for separation and immobilization. Also the membrane should be relatively inert to the biomolecule that one is trying to isolate. For the binding of proteins, for example, the filter membrane is preferably a low protein binding, amino acid free, low molecular weight cut-off material, such as PLGC cellulosic discs made by Millipore Corporation, part No. PLGC 01400. The filter membrane is to allow low molecular weight constituents of a sample volume, such as solvents, salts, reagents, et al, to pass into reservoir 21 while retaining high molecular weight components, i.e. proteins. A typical cut-off value is 10 kiloDalton (kD), although higher or lower cut-off values can be used depending on the size of the biomolecules to be immobilized.

A biomolecule-binding support 25, also about 14 mm. in diameter, is positioned adjacent to and on top of the cut-off membrane, and an O-ring 27 is positioned above the binding membrane to prevent leakage around the two membranes. For protein and nucleic acid separations, the preferred biomolecule -binding supports at the present time are the Immobilon TM and Immobilon N TM PVDF transfer membranes described above, respectively. Those skilled in the art will appreciate that in the general case, the particular support material should be chosen according to the particular kind of biomolecule to be immobilized, and that the material should have a particular affinity for that biomolecule. That affinity could be due to different kinds of binding between the materials, eg. hydrogen bonding, or covalent bonding, or due to Van Der Waals forces, or even ligand-receptor binding systems of various kinds such as with antigen-antibody reactions, biotin-aviden systems, carbohydrate-lectin systems or enzyme-substrate type interactions. Also, in the preferred mode, it is desirable to select a support such that the binding be easily reversed under specified conditions, so that immobilized sample can be removed from the support for subsequent processing.

In the preferred embodiment, a sample tube 29 with a flanged end 31 fits into sample cavity 15 over the O-ring, the biomolecule-binding membrane, and the cut-off membrane. The flanged end contacts the O-ring in assembly, and urges the O-ring and two membranes against the bottom of the sample cavity in the filter base. There is a cap 33 for capping the open end of the sample tube and two clips 35 and 37 for holding the assembly together while processing. The elements described, with the exception of the membranes and the O-ring, are molded plastic materials, selected to be inert to the chemicals used in the procedures described.

Figure 2:
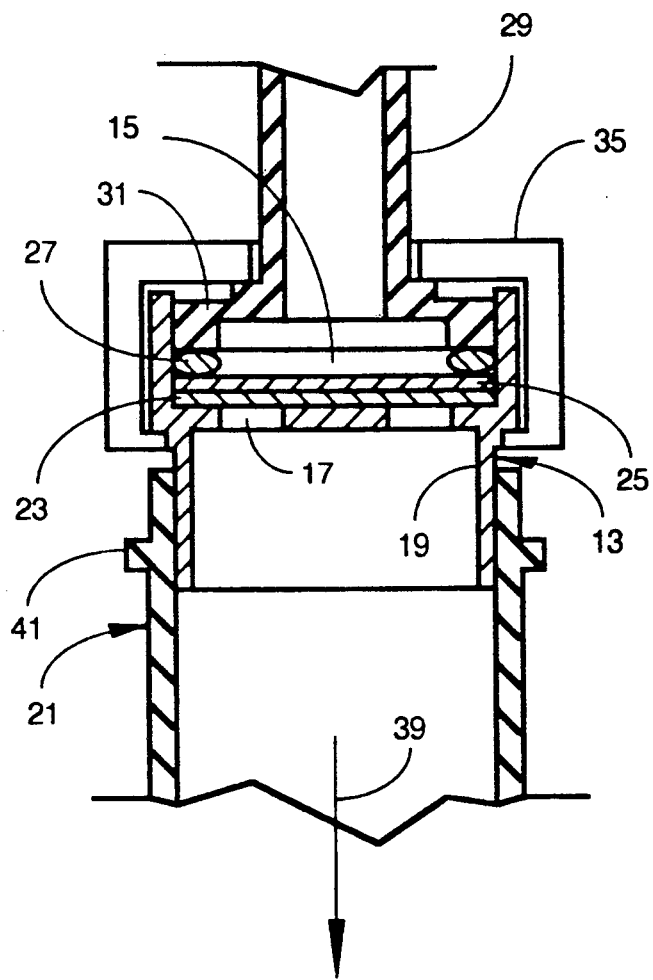
FIG. 2 is a section view through the vertical centerline of the apparatus of FIG. 1, shown assembled.

FIG. 2 is a partial elevation section through the center of microfuge assembly 11, assembled. The assembly is shown held by clip 35 such that flange 31 compresses O-ring 27 urging the peripheral edges of the membranes together and against the bottom of sample cavity 15. A sample is placed in sample tube 29 on the membrane and the assembly is centrifuged in a swinging bucket rotor such that the force of centrifugation is in the direction of arrow 39. The assembly is held in the swinging bucket rotor against shoulder 41 so that the force of centrifugation tends to hold the assembly together.

A sample in the sample tube during centrifugation is forced against the membranes in the sample cavity, and low molecular weight materials pass through both membranes, pass through the openings in the base, such as opening 17, and are collected in reservoir 21. High molecular weight components are prevented from passing the cut-off membrane, and therefore retained in the sample cavity of the filter base. The retained sample material is concentrated in high molecular weight components, i.e. biomolecules, and moreover retained in intimate contact with the biomolecule binding membrane. Additionally, the force of centrifugation urges the concentrated sample material into and throughout the pores of the binding membrane. This is quite unlike a conventional blotting procedure, where the sample material is brought into intimate contact with the internal surface areas of the binding membrane's matrix principally by the relatively small forces of capillary action. In the case of electroblotting, the electrophoretic force aids in bringing the proteins into intimate contact with the membrane's matrix.

The compression of the O-ring around the periphery of the membranes in the apparatus prevents leakage of sample material around the outside of the membranes and assures that all material must pass through the membranes or be retained. It is believed that the concentration of the sample in the vicinity of the binding membrane, leaving the retained portion rich in the biomolecules of interest, and the action of the force of centrifugation in urging the concentrated retained material into and throughout the binding membrane is responsible for the measurably greater efficiency of capture, greater yield, and shorter processing times than experienced with conventional methods.

Figure 3:
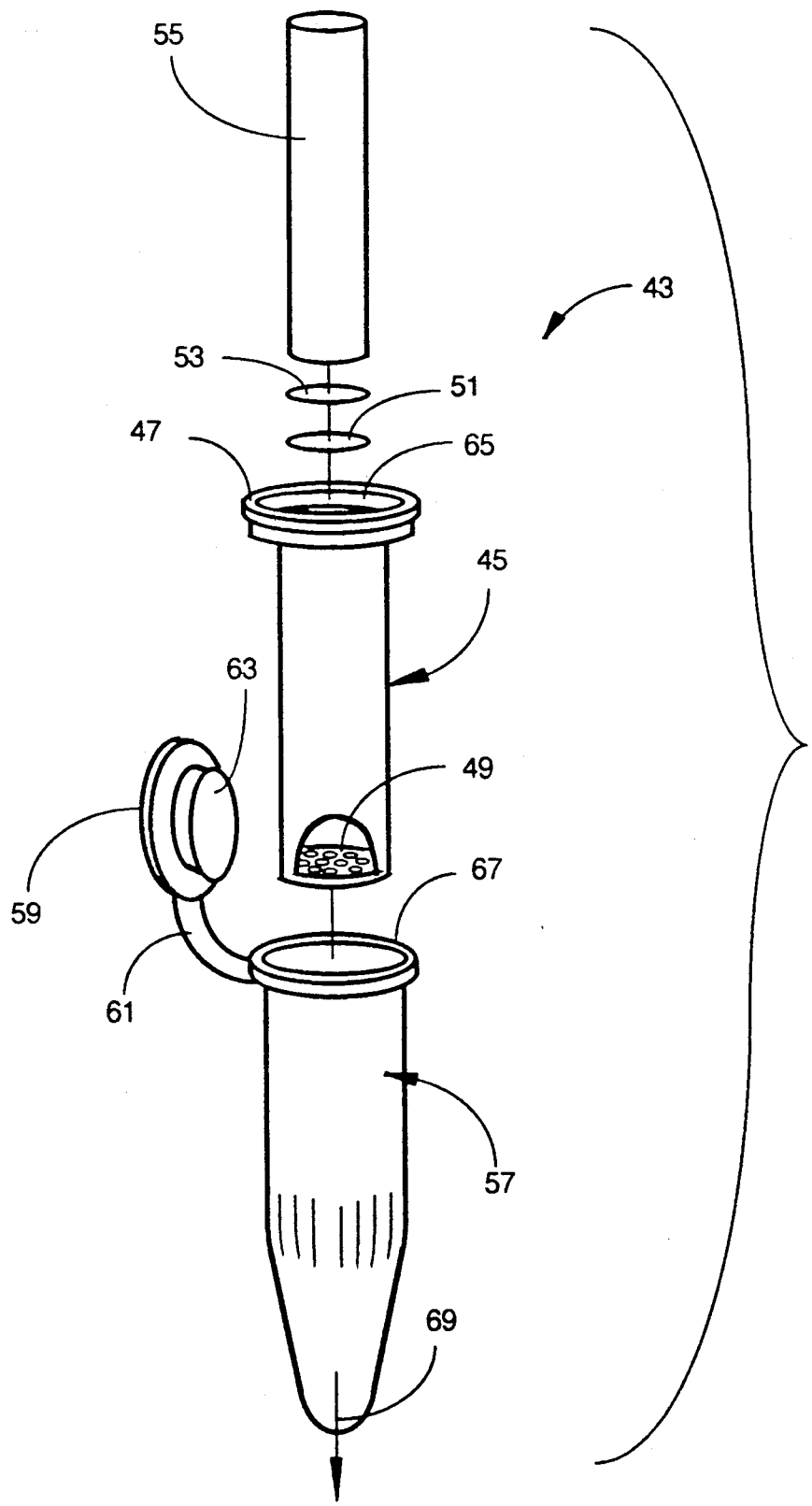
FIG. 3 is an exploded perspective view of an apparatus according to an alternate preferred embodiment.

FIG. 3 in an exploded perspective view of another microfuge assembly according to an alternative preferred embodiment. Microfuge assembly 43 is for relatively small amounts of biomolecule -bearing sample solutions, generally smaller than 10 micrograms, and is configured for processing in a swinging bucket rotor similar to assembly 11 of FIG. 1. Microfuge assembly 43 incorporates 5.5 mm diameter discs.

Filter base 45 is substantially cylindrical with an open flanged end 47 and a partly closed end 49 which has a pattern of openings to allow materials to pass through end 49. In the preferred mode, a 5.5 mm diameter cut-off membrane 51 fits into the filter base against end 49 and a binding support 53, also 5.5 mm diameter, fits into the filter base on top of membrane 51. For protein and nucleic acid immobilizations, the preferred cut-off membrane is of the same PLGC material as used for microfuge assembly 11 and the biomolecule-binding support is of the PVDF material described for the microfuge assembly 11 for protein and nucleic acid immobilizations.

Also, in the alternative preferred embodiment, a cylindrical sample tube 55 of about 5 mm outside diameter and about 4 mm inside diameter fits into filter base 45 such that one end contacts the binding membrane on top of the cut-off membrane against the partially closed end of the filter base. With the sample tube and membranes in place, the filter base fits into a collector reservoir 57 that has a snap cap 59 retained by a thin strap 61. The snap cap has a plug portion 63 that snaps into opening 65 of the filter base in assembly, and urges against one end of sample cylinder 55, urging the other end of cylinder 55 against the membranes and the partially closed end of the filter base. The materials of the elements of microfuge assembly 43, except the membranes, are typically of molded plastic, like those of assembly 11.

The pressure supplied by the snap cap urging the sample cylinder against the membranes makes a seal around the outer periphery of the membranes so that sample material placed inside the sample cylinder is forced during centrifugation to pass through the membranes or be retained. No material can leak around the membranes into the collector reservoir. The assembly is mounted in a swinging bucket rotor for centrifugation by shoulder 67 of reservoir 57. The force of centrifugation is in the direction of arrow 69. The force of centrifugation forces low molecular weight components of a sample mixture to pass through both membranes, the partly closed end of the filter base, and into the collector reservoir.

Components with molecular weight above the cut-off number of the cut-off membrane, i.e. biomolecules, are retained in intimate association with the binding support. Removal of lower molecular weight components increases the concentration of higher molecular weight components in the sample material retained. It is believed that the increased concentration of biomolecules and the induced intimate contact with the binding membrane is responsible for greater efficiency of capture, greater yield, and shorter processing times than experienced with conventional methods, just as in the centrifugation of samples in microfuge assembly 11.

The apparatus described with the aid of FIG. 1, FIG. 2, and FIG. 3 are partly commercially available assemblies for filtration by centrifugation, and are altered for operation according to the invention. Alterations include the use of a cut-off membrane and a binding support, in combination, and provision of peripheral sealing to prevent leakage around the membranes during centrifugation. Centrifugation is convenient and is the preferred method of urging sample material through the membranes, but there are other ways that pressure might be applied without departing from the spirit and scope of the invention. For example, an apparatus similar to microfuge assembly 11 could be used with cap 33 replaced with a tubing to conduct inert gas from a pressure source. Inert gas under pressure could be used to urge sample material through the membranes in such an apparatus. Also, the sample tube could be fitted with a piston and the piston used to induce pressure to force part of the sample through the membranes. Similarly, vacuum (or suction) with an appropriate configuration may also be employed for forcing the sample through the binding membrane.

An exemplary procedure for binding proteins using microfuge apparatus 11 is as described in the following paragraphs:

After PLGC and PVDF membranes are cut to size (14 mm diameter) the PLGC membrane is soaked in DI water for 20 minutes and a PVDF membrane, which is hydrophobic, is soaked in 100% methanol for at least 5 minutes.

After soaking, the PLGC membrane is placed in the filter base "shiny side up" followed by the PVDF membrane. The O-ring is placed on the upper (PVDF) membrane using clean forceps, the sample tube is inserted onto the O-ring, and the clips are assembled to lock the sample tube into the filter base, compressing the O-ring.

After assembly, the membranes are wet with 200 micro-liters of DI water and the sample is carefully added to the PVDF membrane surface. If the PVDF membrane appears to have dried before the sample is added, 200 micro-liter of 100% methanol is added, the excess is removed, then the DI water and the sample are added, and the cap is placed on the sample tube.

Following addition of the sample, the assembly is inserted into the collector reservoir, placed in a swinging bucket rotor, and centrifuged (ca. 3000×g) to dryness. Centrifugation times vary somewhat, depending on the volume and the initial concentration of the sample, but a time from 1 to 3 hours is typical. After first centrifugation, the sample is washed to remove salts and other contaminants by addition of 1 mL of 20% methanol and centrifuged again to dryness. The wash is repeated so that at least 3 mL of 20% methanol passes through the sample. If the membranes are not dry after the washing steps, they are vacuum dried or exposed to air to dryness. Another nice feature of this centrifuging approach is that sample is never lost. Hence, sample that was not immobilized and passed through both membranes can be recentrifuged as described to capture those biomolecules that were not captured earlier.

The PVDF disc with sample attached is ready after the washing and final drying for sequencing, amino acid analysis, or fragmentation, or any combination of these or other analysis procedures. The PVDF membranes can also be stored, for example in a dessicator at 4 degrees C., for future use. Membranes should be completely dry prior to the washing steps described above, otherwise unbound proteins may be washed away during subsequent centrifugation.

Protein recovery has been quantified using microfuge assembly 11 and the centrifugation procedure described above, through experiments with ratio-labeled proteins. For the recovery experiment, methylated-$^{14}$C labeled proteins purchased from New England Nuclear and other suppliers were used, and free $^{14}$C was removed by gel filtration onto PVDF membrane prior to centrifugation. The proteins used in the experiment were myosin, phosphorylase-B, methemoglobin, ovalbumin, carbonic anhydrase, casein, Beta-lactoglobulin, cytochrome-C, aprotinin, and insulin. After binding to PVDF was accomplished, the relative amounts of labeled proteins in the binding membrane, the cut-off membrane, and in the filtrate and collector reservoir were measured. Both membranes were placed in separate scintillation vials containing 0.5 mL extraction buffer (62 mM Tris-HCL, 2% NP40, 3% SDS, 6M Urea, 0.2% Beta-mercaptoethanol, and 10% glycerol, pH 6.8) and tightly sealed. Vials were incubated at 100 degrees C. for about 20 minutes and allowed to cool at room temperature. Scintillation cocktail (10 mL) Econoline TM was added prior to $^{14}$C counting.

Figure 4:
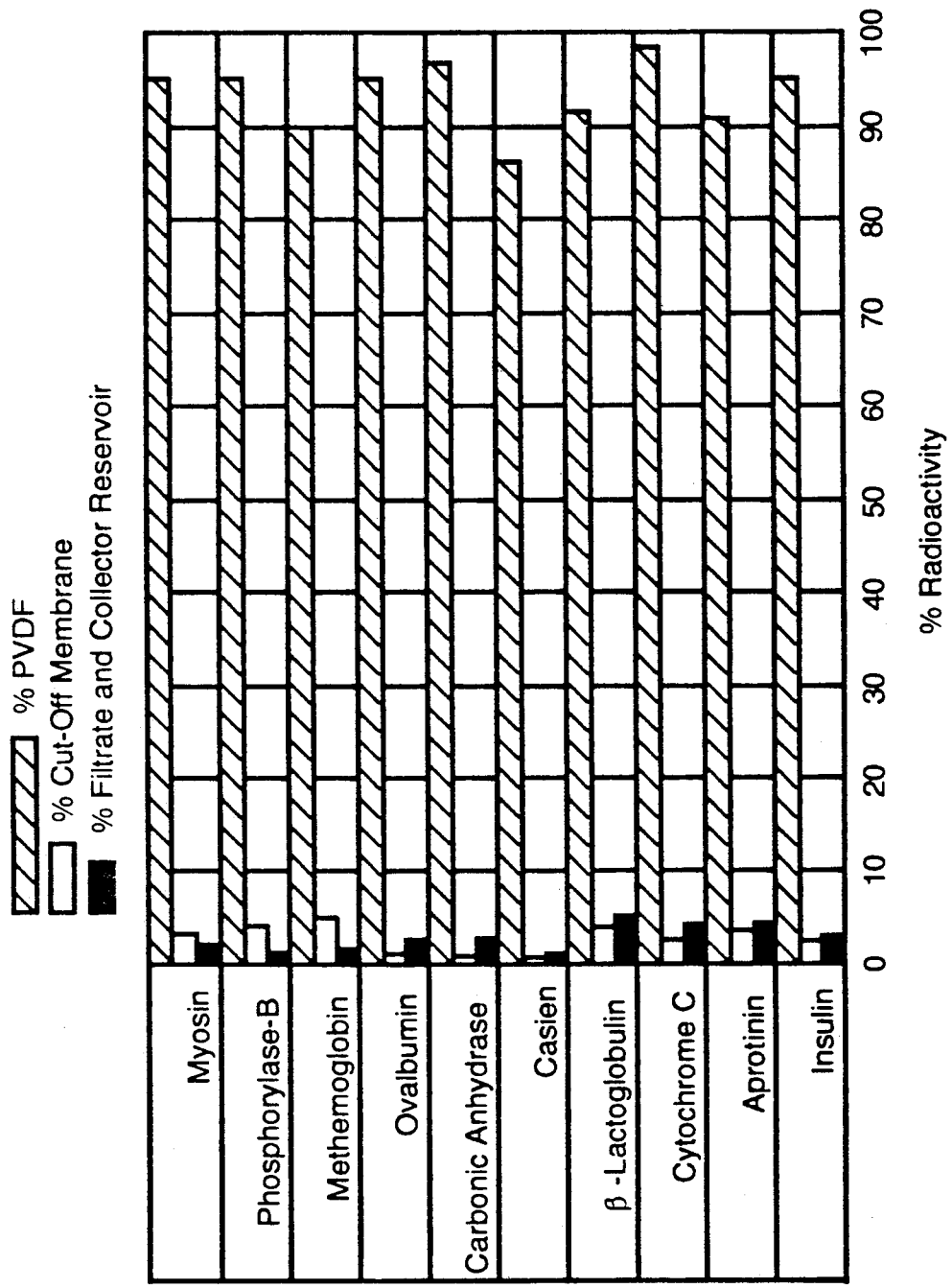
FIG. 4 is a bar chart showing the results of a test of the apparatus of FIG. 1 using radioactively labeled proteins.

The distribution of radioactivity in the filtrate and collector reservoir, the cut-off membrane, and the PVDF membrane is shown in FIG. 4. Less than 10% of the total counts were found in the filtrate and collector reservoirs. Extraction of radioactivity is a function of time and varies from protein to protein. For example, methemoglobin, casein, or aprotinin require 20 minutes at 100 degrees C. for 90% recovery, while only 10 minutes is required for other proteins.

Those skilled in the art will appreciate the utility of using these two types of filters together, i.e. molecular sieve to concentrate the materials of interest and a binding membrane to capture those materials, for many kinds of biomolecules other than proteins. As has been already pointed out, nucleic acids are of particular importance, and binding membranes have already been developed and used not just for immobilization but also for hybridization experiments. Also, a large number of laboratories are presently performing experiments to investigate the interaction of DNA-binding proteins. The identification of these biomolecules are directly involved in gene regulation at the nuclear (chromosomal) level and require specific DNA promoter regions located at the N-terminal region of the untranslated DNA. The following example is a description of another experimental procedure where this combination of filters is useful in the case of DNA-binding proteins. Before proceeding, it should be understood that thyroid hormone is known to bind to growth hormone promoter sites. Rat pituitary cells grown in culture were used as a source of RNA and protein. Specific protein from the nuclear pituitary cell extract (GH1) was centrifuged onto a number of binding membranes to adsorb the protein for later use in the binding assay. This was performed in a low salt buffer (50 mM NaCl) so as to optimize binding conditions, For this portion the preferred binding membrane is ProBlott TM on PGLC, although Immobilon, nitrocellulose, DEAE-cellulose, or derivatized nylon, for example, could also be used in the combination. Use of the two-filter combination of the invention greatly facilitates the percentage of protein bound. Synthetic oligonucleotides (18 base pairs) of the promoter site to the DNA that binds to the receptor of thyroid hormone are than labeled with $P^{32}$ (nick translated) and centrifuged onto some of the binding membranes having the growth hormone extract attached thereto. Washing and centrifugation with high salt concentrations (1–1.5M NaCl) is sequentially performed to remove non-specifically bound labeled DNA. The radioactivity of the samples that have been treated with DNA can then be compared with the samples that have not been treated with DNA as a control quantitate the assay. Finally, if desired, the protein can be subjected to chemical cleavage (ie. CNBr), eluted from the membrane, purified and sequenced while monitoring the radioactivity.

As another example, the apparatus of the invention can accomodate applications for DNA isolation and amplification of selected genomic DNAs, which provides for a very quick and easily performed screening tool. Serum from patients is centrifuged to a clear plasm and is treated with RNAse and proteinase K to extract RNA and protein. Sample is then centrifuged in the described apparatus using a derivatized nylon membrane for the binding support. The membrane is then washed with an appropriate 1X buffer and then eluted off (the affinity for binding DNA is generally much less for nylon than other membrane supports) in a high salt buffer (e.g. 2×) and then either fragmented or subjected directly to PCR to amplify the selected DNAs for cloning/sequencing etc. As an alternative, the DNA could be subjected to PCR in situ on the nylon support.

It will be apparent to one skilled in the art that there are many changes that may be made in the apparatus and methods described in the preferred embodiments without departing from the spirit and scope of the invention. The apparatus described, for example, is based on apparatus commercially available, and alterations and additions were made to existing systems. The use of available apparatus as a starting point was merely a convenience and is not meant to be a restriction on the concept of the invention, since other apparatus could be provided in place of the available apparatus. The sizes of the particular components chosen are for convenience also, and were chosen to accomodate sample sizes frequently encountered. Other sizes may also be useful. Similarly other filter cut-offs may also be useful, depending on the size of the biomolecules to be immobilized. For example, although low molecular weight cut offs have not been investigated in detail, cut off filters as low a 3 kD have been found in practice to be particularly useful as well. Centrifugation was found to be a convenient and efficient way to cause the filtration and concentration to take place, however, as indicated earlier, other ways of forcing the samples through the membranes may be suitable in other embodiments. It should also be appreciated that the apparatus and method are applicable to other kinds of biomolecules as well, not just proteins and nucleic acids, for example lipids and carbohydrates, including complexes and conjugates thereof. Similarly, there are many different binding supports that can be used depending on the particular biomolecule to be bound. Some examples of these binding support membranes include derivatized glass bends, derivatized nylon, parchment, macrocyclic polyethers, polyvinylbutyral resins, polyvinylalcohol-collagen, polyvinylidene difluoride, and other polymers. There are many other alterations that may be made without departing from the spirit and scope of the invention.

What is claimed is:

1. An apparatus for adsorbing biomolecules from a sample volume comprising:
    a cut-off filter membrane for filtering and selectively passing components of said sample volume according to size;
    adsorption membrane means adjacent said cut-off filter membrane for selectively adsorbing said biomolecules;
    filter holding means having a through passage, said filter holding means for supporting said cut-off filter membrane and said adsorption membrane means, with said adsorption membrane means overlying said cut-off filter membrane;
    a sample tube for receiving said sample volume;
    sealing means between said sample tube and said adsorption membrane means such that any component of said sample volume must either pass through said adsorption membrane means, said cut-off filter membrane and said filter holding means, or be retained in said sample tube;
    force application means for urging said sample volume in said sample tube onto said adsorption membrane means and forcing components of said sample volume through said cut-off filter.

2. An apparatus as in claim 1 wherein said adsorption membrane means comprises a material having a affinity for the biomolecule to be adsorbed.

3. An apparatus as in claim 1 wherein said sealing means comprises an O-ring and O-ring compression means, said O-ring positioned between said sample tube and said adsorption membrane means, and said O-ring compression means urging said filter holding means, said cut-off filter membrane, said absorption membrane means and said sample tube together.

4. An apparatus as in claim 1 wherein said sample tube is a cylinder and said sealing means comprises a compression means for urging one end of said sample tube against said adsorption membrane means and urging said filter holding means, said cut-off filter membrane, said adsorption membrane means and said sample tube together.

5. An apparatus as in claim 1 wherein said force application means comprises attachment means on said apparatus, said attachment means configured for mounting said apparatus in a centrifugation rotor.

6. A method for adsorbing biomolecules from a sample volume comprising the steps of:
    urging said sample volume against a biomolecule-adsorbing membrane that is in contact with a cut-off filter membrane such that said sample volume will pass through said biomolecule-absorbing membrane before passing through said cut-off filter membrane.

7. The method of claim 6, wherein said biomolecules comprise a nucleic acid, further comprising the step of exposing said nucleic acid to a polymerase chain reaction for amplification after said adsorption to said support membrane.

8. A method of performing a binding assay for a DNA-binding protein, comprising:
    urging a sample volume containing said protein against a protein-adsorbing support membrane that is in contact with a cut-off filter membrane such that sample volume will pass through said protein-adsorbing support membrane before passing through said cut-off filter membrane, thereby leaving said protein bound to said protein-adsorbing support membrane;
    urging a second sample volume containing DNA against said protein-adsorbing support, thereby binding said DNA to said protein bound to said protein-adsorbing support;
    removing DNA not specifically bound to said proteins; measuring the amount of DNA bound to said proteins.

9. A method for binding biomolecules from a sample volume comprising the steps of:
    placing a cut-off filter membrane on a filter base, said filter base having a through passage;
    placing a biomolecule adsorbing membrane over said cut-off filter membrane; and
    urging said sample volume against said biomolecule absorbing membrane by centrifugation in a centrifuge apparatus.

10. A method for binding biomolecules from a sample volume comprising the steps of:
    placing a cut-off filter membrane on a filter base, said filter base having a through passage;
    placing a biomolecule adsorbing membrane over said cut-off filter membrane;
    sealing a sample tube against said biomolecule adsorbing membrane; and
    introducing said sample volume into said sample tube.

* * * * *